(12) United States Patent  
Chow

(10) Patent No.: US 6,944,490 B1
(45) Date of Patent: Sep. 13, 2005

(54) APPARATUS AND METHOD FOR POSITIONING AND DELIVERING A THERAPEUTIC TOOL TO THE INSIDE OF A HEART

(75) Inventor: Mina Chow, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 61 days.

(21) Appl. No.: 10/254,621

(22) Filed: Sep. 25, 2002

(51) Int. Cl.[7] .................................................. A61B 5/04
(52) U.S. Cl. ....................................... 600/374; 606/47
(58) Field of Search ................................ 600/374, 439, 600/509, 508, 104, 106, 201, 204, 205, 206, 600/208–210, 219; 606/45, 47, 167, 170, 606/186; 607/122

(56) References Cited

U.S. PATENT DOCUMENTS

| | | | |
|---|---|---|---|
| 4,699,147 A | 10/1987 | Chilson et al. | 128/642 |
| 5,406,946 A | 4/1995 | Imran | 128/642 |
| 5,628,313 A | 5/1997 | Webster, Jr. | 128/642 |
| 5,690,611 A | 11/1997 | Swartz et al. | 604/53 |
| 5,697,377 A | 12/1997 | Wittkampf | 128/696 |
| 5,722,401 A | 3/1998 | Pietroski et al. | 128/642 |
| 5,740,808 A | 4/1998 | Panescu et al. | 128/662.06 |
| 5,908,446 A | 6/1999 | Imran | 607/122 |
| 6,063,082 A | 5/2000 | DeVore et al. | 606/45 |
| 6,070,094 A | 5/2000 | Swanson et al. | 600/374 |
| 6,156,018 A | 12/2000 | Hassett | 604/281 |

Primary Examiner—Beverly M. Flanagan
(74) Attorney, Agent, or Firm—Squire, Sanders & Dempsey

(57) ABSTRACT

A medical device and method are provided for positioning and supporting a therapeutic tool within the heart or other body cavity. The device has a tubular member through which a cage can be extended. The cage supports the positioning and delivery of a tool to a targeted treatment or diagnosis area within the heart or other body cavity. Markers on the device facilitate accurate positioning and delivery of the tool.

24 Claims, 9 Drawing Sheets

APPARATUS AND METHOD FOR POSITIONING AND DELIVERING A THERAPEUTIC TOOL TO THE INSIDE OF A HEART

BACKGROUND

The invention relates generally to the field of medical devices used to position and deliver therapeutic or diagnostic tools into the interior of a patient. More particularly, the invention relates to medical devices used to position and deliver a therapeutic tool to a treatment area within a patient's heart for the treatment of heart disease.

Heart disease is a significant health problem and a common cause of death. A common form of heart disease is ischemic heart disease, a condition in which parts of the heart muscle, or myocardium, do not receive an adequate supply of blood. Typically, this condition occurs when the arteries that carry blood to the myocardium become clogged by plaque build-up on their inner walls. The clogged arteries hinder blood flow, and the myocardium in the ischemic area is deprived of oxygen and other nutrients.

A number of treatments for heart disease involve direct interaction of a therapeutic tool with the wall of the heart. For example, in transmyocardial revascularization (TMR), therapeutic tools such as mechanical coring devices, lasers, or RF electrodes are used to create channels in the myocardium. The channels allow blood to flow directly from the ventricle into the ischemic area to reperfuse the tissue.

To minimize trauma to the patient, these treatments are often performed from the inside of the heart. A catheter that supports the therapeutic tool is inserted into an artery and guided through the vasculature into the heart chamber. The therapeutic tool is then used to perform the treatment on the inner wall of the heart.

For these treatments to be most effective, however, the therapeutic tool must be accurately positioned against the wall of the heart to deliver the therapy to the target location. For example, for TMR procedures, channels are made either directly into the ischemic area of the myocardium, or into the healthy tissue at the edge of the ischemic area. Therefore, the therapeutic tool used to create the channel must be placed at a location within or at the edge of the ischemic tissue. The therapeutic tool may cause unnecessary damage to healthy tissue should the therapeutic tool not be precisely placed at the target site or if the therapeutic tool lacks a substantial degree of control.

Current methods for positioning such tools can be cumbersome and imprecise. For example, U.S. Pat. No. 6,070,094 issued to Panescu et al. describes a method for positioning an ablation electrode. An array of electrodes is inserted into a heart chamber. The array is used to guide a moveable ablation electrode to a targeted site by emitting and sensing electrical and ultrasound energy. The method requires a specialized processing system that uses the sensed energy to generate an output locating the ablation electrode relative to the electrode array. A further problem is that, once the therapeutic tool is accurately placed, it must be supported and held in the proper location for the duration of the treatment. Because the heart is beating and filled with flowing blood, keeping the therapeutic tool in the proper location can be difficult. Accordingly, a device is provided for addressing the aforementioned problems.

SUMMARY

A medical device and method are provided for positioning and supporting a therapeutic or diagnostic tool for use in a body cavity or body organ of a patient. Using the device, a therapeutic tool can be precisely positioned at a selected treatment site and securely held at the treatment site for the duration of the treatment. Accurate positioning of the therapeutic tool using the device of the present invention is accomplished in conjunction with imaging equipment commonly available in hospitals. Additionally, the device and method of use are compatible with future imaging techniques contemplated herein as well as imaging techniques not yet readily available for use.

In one embodiment, a medical device has an elongate tubular member for inserting into a body cavity or organ of a patient. Additionally, the device has at least two support arms capable of extending out from and retracting into the distal end of the elongate tubular member. The support arms converge at the distal end of the support arms and are outwardly bow-shaped when extended out from the elongate tubular member. Further, a tool for performing a therapeutic or diagnostic function extends at least partially along one of the support arms.

A method of one embodiment involves performing a therapeutic or diagnostic treatment by inserting a catheter into the patient and extending a set of support arms out from one end of the catheter. The support arms bow in an outward direction to anchor the catheter to the desired area of treatment. Further, a therapeutic or diagnostic tool is extended from a conduit disposed at least partially along one of the support arms to perform a therapeutic or diagnostic procedure.

DETAILED DESCRIPTION

Figure 1:
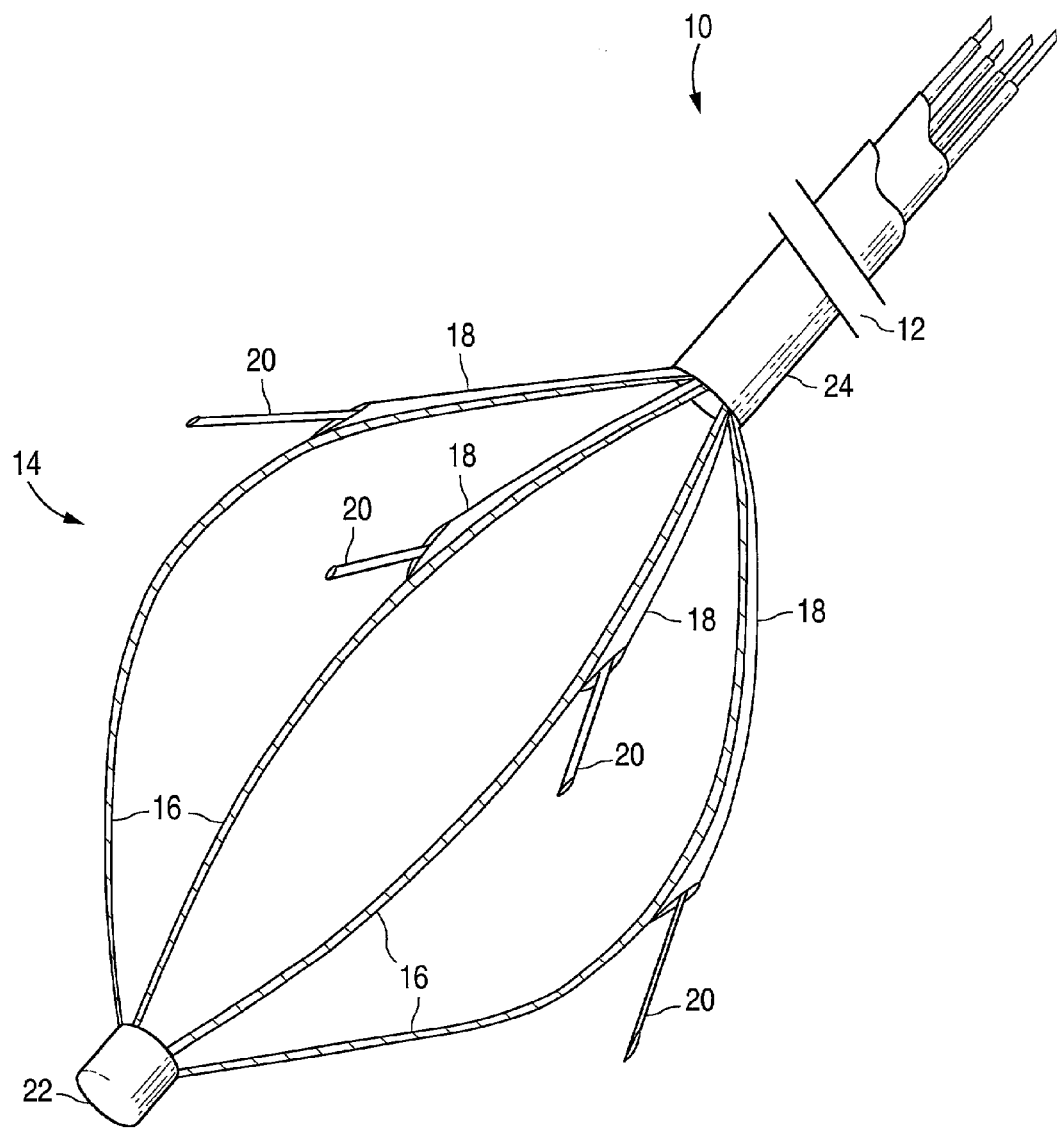
FIG. 1 is a partial perspective view of one embodiment of the invention.

FIG. 1 illustrates a perspective view of one embodiment of the invention. A catheter 10 includes an elongated tubular member 12 having support arms 16 extending out from the distal end of elongate tubular member 12 and configured for being expanded relative to the longitudinal axis of elongate tubular member 12. Support arms 16 form a cage, generally illustrated by reference number 14. Tools 20, which are slidably disposed within conduits 18, can be extended out from or contracted back within conduits 18. Conduits 18 are coupled to at least a region of support arms 16. FIG. 1 illustrates a total of four support arms 16, conduits 18, and therapeutic tools 20, but any number of support arms 16, conduits 18, and therapeutic tools 20 is conceivable provided that the overall cross-section of catheter 10 is kept to a clinically-useful dimension. FIG. 1 further illustrates that the distal ends of support arms 16 are attached to a tip 22. Support arms 16 can be made from a flexible material such that cage 14 is capable of being expanded from a contracted position and subsequently re-contracted into its original contracted position. Since conduits 18 are attached to support arms 16, expansion of cage 14 can be accomplished by pushing conduits 18 along the longitudinal axis of tubular member 12. FIG. 1 illustrates cage 14 in an expanded position.

Figure 2A:
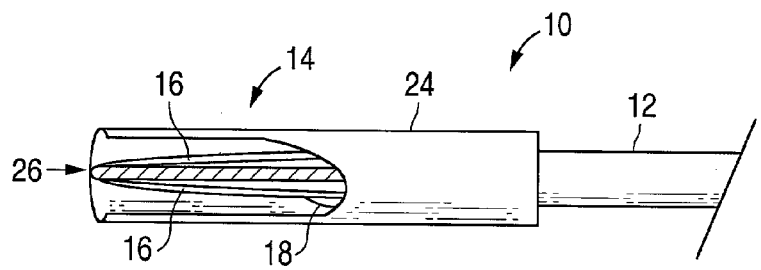
FIG. 2A is a partial, sectional side view of one embodiment of the invention with a cage in a retracted state.
Figure 2B:
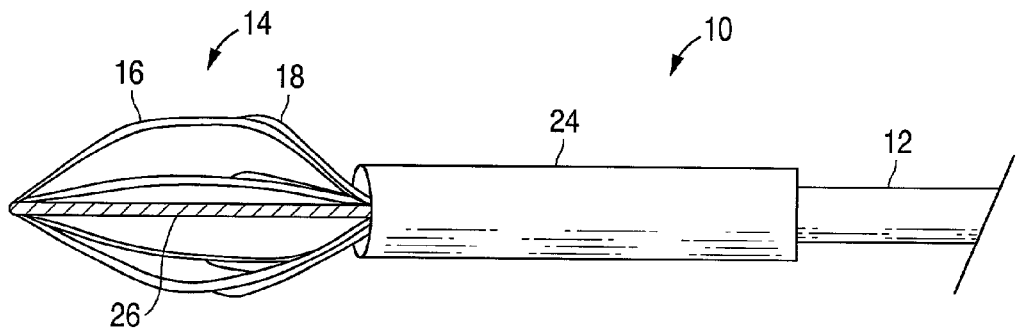
FIG. 2B is a side view of one embodiment of the invention with the cage in a deployed state.

FIG. 2A illustrates a side view with a partial cut-away of another embodiment of the invention, which includes a shaft 26. The distal ends of support arms 16 are attached to the distal end of shaft 26. In FIG. 2A, support arms 16, which define cage 14, are shown in a contracted state within a holder 24. FIG. 2B illustrates the same embodiment of the invention as FIG. 2A, but support arms 16 are shown in an expanded state beyond the distal end of holder 24.

FIGS. 2A and 2B illustrate the relationship between the expanded and contracted state of cage 14 and shaft 26. The distal ends of support arms 16 are attached to shaft 26, which runs along the longitudinal axis of catheter 10. Shaft 26 can be hollow to accommodate a guidewire (not pictured), which is a device well-known in the art and often used in PTCI procedures. When conduits 18, and, if present, shaft 26, are slid in the proximal direction along the longitudinal axis of elongate tubular member 12, the distance between support arms 16 and shaft 26 decreases such that cage 14 retracts into holder 24 to assume a retracted position.

Figure 2C:
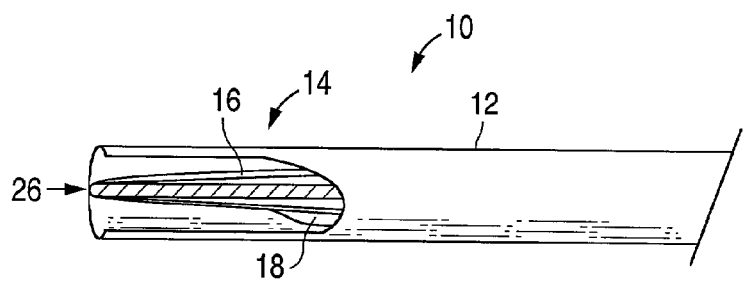
FIG. 2C is a partial, sectional side view of another embodiment of the invention.

In the embodiment illustrated in FIG. 2A, cage 14 in its contracted state is housed within holder 24 rather than within elongate tubular member 12 so that the diameter of elongate tubular member 12 may be minimized. In contrast, FIG. 2C illustrates a side view with a partial cut-away of an embodiment of the invention in which cage 14 is shown in a contracted state within elongate tubular member 12. The use of holder 24 to house contracted cage 14 depends at least on the diameter of cage 14 in the contracted state. If the diameter of cage 14 in the contracted state is sufficiently small relative to the desired diameter of elongate tubular member 12, then holder 24 may be unnecessary. Generally, smaller diameter devices are desirable for access into small or tortuous body cavities.

Figure 3A:
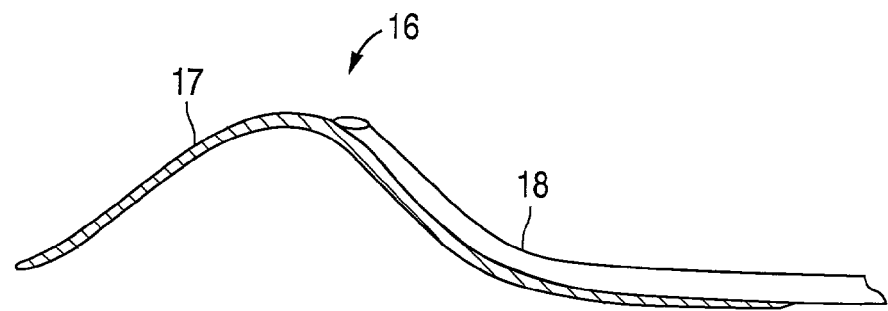
FIGS. 3A, 3B and 3C are side views of support arms in accordance with various embodiments of the invention.
Figure 3B:
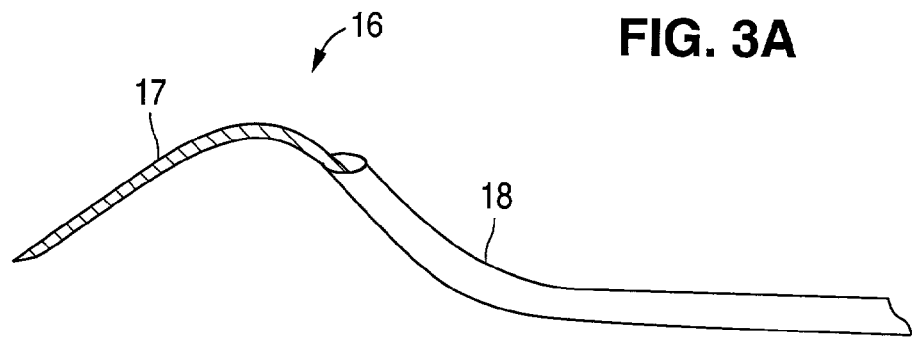
Figure 3C:
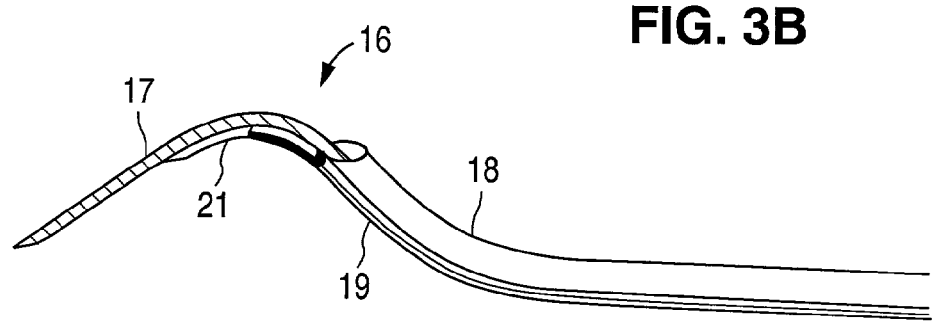

FIGS. 3A, 3B, and 3C are side view illustrations of different embodiments of support arms 16. Support arms 16 can be formed from elastic materials, such as metals or polymers. The elasticity of the material from which support arms 16 are formed allows cage 14 to expand from and retract into holder 24. Metal materials suitable for forming support arms 16 include, but are not limited to, spring steel or a nickel titanium alloy such as ELASTINITE® (Advanced Cardiovascular Systems, Inc., Santa Clara, Calif.). Support arms 16 can be formed from conventional wire materials or ribbon materials, or from a wire or ribbon that has been pre-formed into a bowed shape.

In one embodiment of support arm 16 illustrated in FIG. 3A, a pre-formed ribbon 17 is attached to conduit 18 using an adhesive such that an open end of conduit 18 terminates at a point along ribbon 17 and does not extend to the distal end of ribbon 17. Conduit 18 can be made from a polymeric tube. In an alternate embodiment illustrated in FIG. 3B, instead of using a tube, conduit 18 can be constructed from a thin strip of polymer folded in a semi-circle, the ends of which are attached to ribbon 17 using an adhesive. In a third embodiment illustrated in FIG. 3C, support arm 16 includes a reinforcing arm 19 which is slidably disposed within a reinforcing lumen 21. Reinforcing lumen 21 runs at least partially along the length of support arm 16, and may terminate proximally of the distal end of support arm 16. The proximal end of reinforcing lumen 21 is accessible to the operator such that reinforcing arm 19 may be inserted in the proximal end of reinforcing lumen 21. Sliding reinforcing arm 19 to the distal end of reinforcing lumen 21 may provide additional stiffness to support arm 16. The distal end of reinforcing lumen 21 may be sealed to prevent fluid leakage into reinforcing lumen 21 from the body.

In each embodiment illustrated in FIGS. 3A, 3B, and 3C, the location of the distal end of conduit 18 can be chosen such that as cage 14 expands, the distal end of conduit 18 is displaced at the maximum distance away from the longitudinal axis of elongate tubular member 12. Because conduit 18 extends along at least a portion of the length of catheter 10, the material used to form conduit 18 should be capable of flexing with catheter 10 to allow insertion through the vasculature or other body passageway. Conduits 18 can be formed from flexible materials such as polymers. Polymeric materials suitable for forming conduits 18 include, but are not limited to, polyethylene or polytetrafluoroethylene, also known as Teflon® (E.I. Du Pont de Nemours and Company, Wilmington, Del.). Suitable polymeric materials should also provide a low friction surface over which tool 20 may slide. Both polyethylene and polytetrafluoroethylene, among other polymeric materials, provide a low friction surface.

Figure 4A:
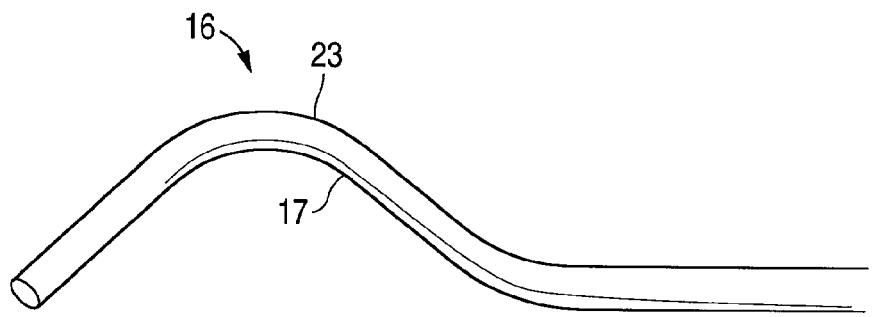
FIGS. 4A, 4B, 4C, and 4D are sectional side views of an embodiment of the invention depicting a method of making a support arm.
Figure 4B:
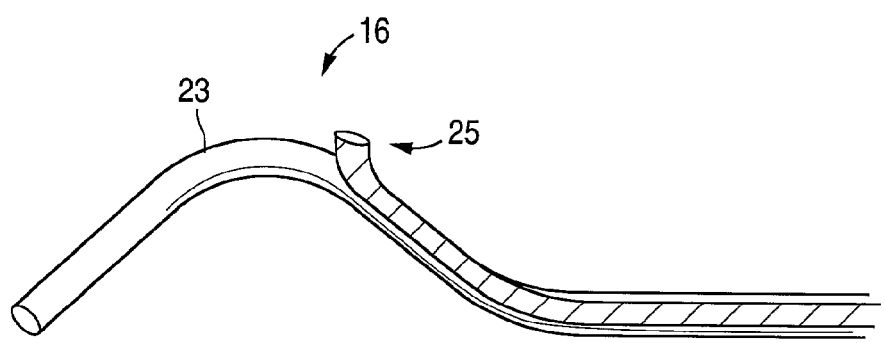
Figure 4C:
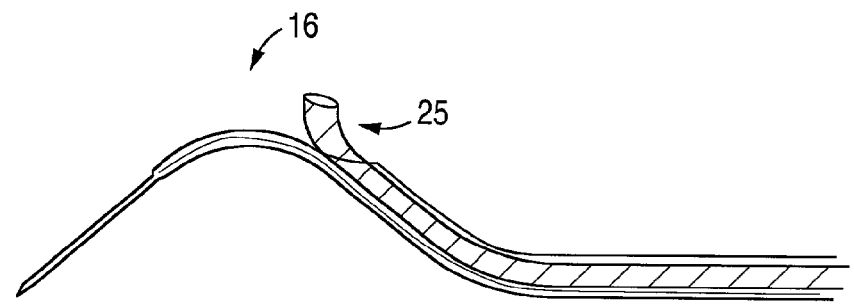
Figure 4D:
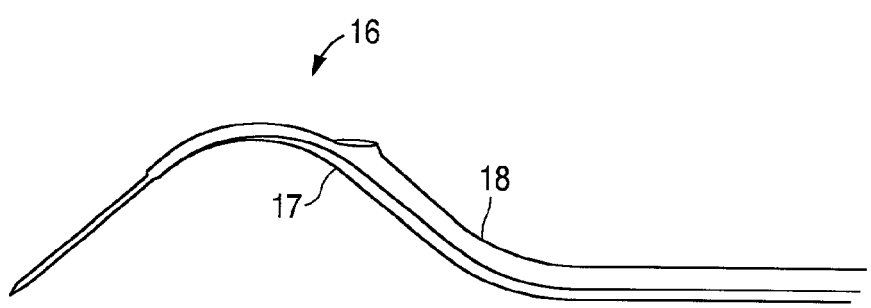

In still another embodiment of support arm 16 illustrated in FIGS. 4A–4D, ribbon 17 of ELASTINITE® can be pre-formed to have a bowed shape. Ribbon 17 can be inserted into a tube 23 made from the polymeric material chosen for use as conduit 18, such as polyethylene, as illustrated in FIG. 4A. An opening in tube 23 is cut at a point on the bowed section of ribbon 17 to create the site that will form the distal end of conduit 18. As illustrated in FIG. 4B, a mandrel 25 is inserted into the opening, over the portion of ribbon 17 in tube 23, and through the length of the tube 23. A heat treatment is applied and the portion of tube 23 not supported by mandrel 25 melts and collapses, securing ribbon 17 inside the section of tube 23 distal to the opening cut in tube 23, as illustrated in FIG. 4C. The portion of tubing supported by mandrel 25 during heat treatment becomes conduit 18 when mandrel 25 is removed, as illustrated in FIG. 4D.

In each of the previously illustrated embodiments, complementary materials may be chosen to form support arms 16 and conduits 18. In other words, the choice of materials for support arms 16 should not unduly reduce the effectiveness of the choice of materials for conduits 18. Further, the method of uniting support arms 16 and conduits 18 must be chosen to provide the required balance of flexibility and strength. Construction of cage 14, which is composed of support arms 16 and conduits 18, requires balancing the flexibility and strength requirements commonly found in the design of intravascular catheters. In addition, cage 14 must be able to flex and maintain its position within the body cavity. When cage 14 is deployed within the ventricle of a heart, it should be strong enough to anchor against the walls of the ventricle but flexible enough to move with the heart as it beats.

Figures 5A, 5B, 5C, 5D, 5E, 5F:
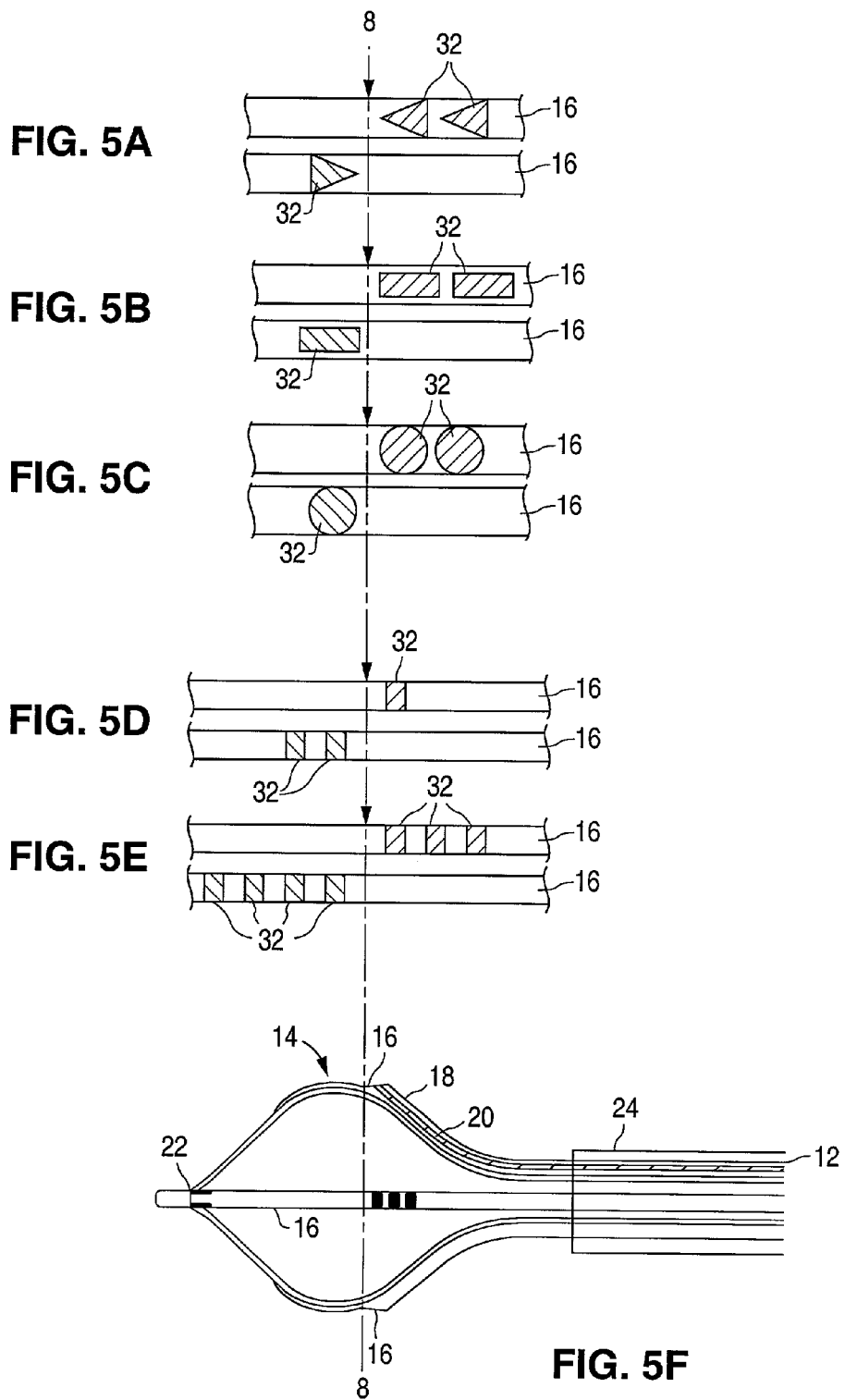
FIGS. 5A, 5B, 5C, 5D, 5E, and 5F are enlarged partial views of a pair of support arms, each figure depicting an alternate embodiment of the invention.

FIGS. 5A–5F illustrate various schemes of marking support arms 16. FIGS. 5A, 5B and 5C illustrate plan views of support arms 16 with markers 32 attached. Dashed line 8 identifies the location of markers 32 on a side elevational view in FIG. 5F, although FIGS. 5A, 5B, and 5C are not in scale with FIG. 5F for the sake of clarity. In the embodiment illustrated in FIG. 5A, marker 32 having a triangular shape is attached to one support arm 16 of a pair of opposing support arms 16. Markers 32 need not have a triangular shape and can include any geometric design suitable for providing visual indication on the device. For example, markers 32 can be square, as illustrated in FIG. 5B, or circular, as illustrated in FIG. 5C. In accordance with one embodiment, each pair of support arms 16 for cage 14 can have a different shape marker 32. The embodiment provides an advantage of allowing one pair of support arms 16 to be distinguished from another pair of support arms 16.

FIGS. 5D and 5E illustrate embodiments of the invention in which markers 32 of the same shape but of different number are used to identify support arms 16. When the shape of markers 32 is used to distinguish between pairs of support arms 16, the visualization device should have sufficient resolution to distinguish the shapes of markers 32 from outside the body. If the hospital has a visualization device of lesser resolution, for example, resolution sufficient to show markers 32 but not sufficient to show the details of the shapes of markers 32, support arms 16 may be distinguished solely by using different numbers of markers 32. In general, a variety of shapes and numbers of markers can be used to identify support arms 16 as long as markers 32 can be visualized and distinguished from outside the body. Possible methods of marker visualization include x-ray fluoroscopy and magnetic resonance imaging.

In the embodiment illustrated in FIGS. 5A–5F, markers 32 are disposed on the outward surface of support arms 16. Alternately, markers 32 can be located on the inward surface of support arms 16. Markers 32 are made from materials capable of being imaged by an external imaging modality. When fluoroscopy is the external imaging mode, markers 32 can be made from a radiopaque material such as gold. Markers 32 can be soldered or welded onto the pre-formed wire or ribbon used to construct support arms 16 and can be further secured by the method that collapses a tube via heat treatment to form support arms 16 and conduits 18. Alternately, markers 32 can be attached to support arms 16 or conduits 18 using an adhesive.

Figure 6:
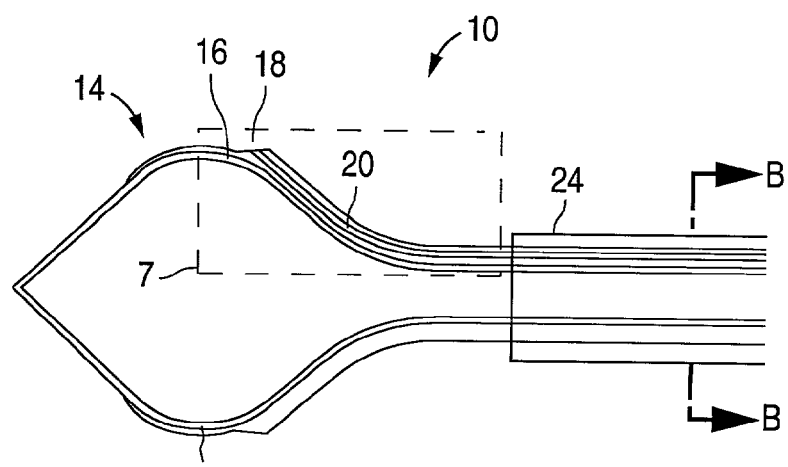
FIG. 6 is a sectional side view of one embodiment of the invention.
Figure 7A:
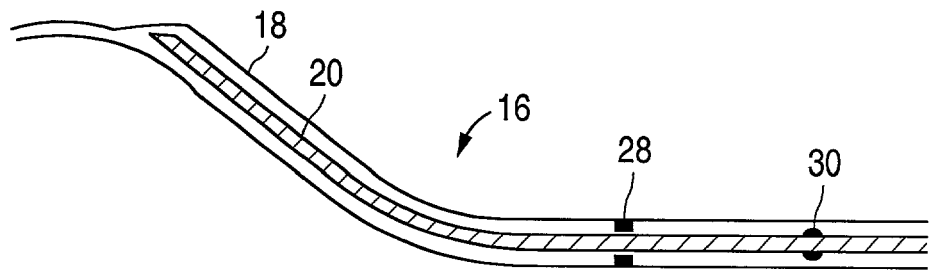
FIGS. 7A and 7B are sectional side views of a conduit of one embodiment of the invention.
Figure 7B:
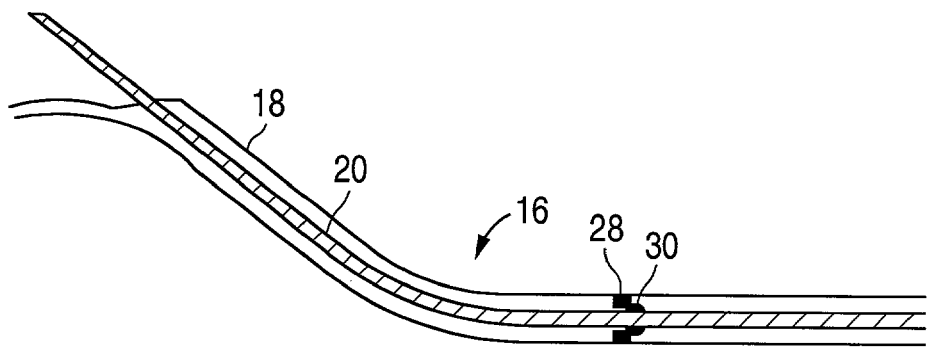

FIG. 6 is a sectional side view of an embodiment of the invention that illustrates the relationship between support arm 16, conduit 18, and tool 20. FIGS. 7A and 7B illustrate an enlarged, sectional side view of the region 7 from FIG. 6. In the illustrated embodiment, FIG. 7A depicts tool 20 disposed completely within conduit 18. FIG. 7B depicts tool 20 extending beyond the distal end of conduit 18. Tool 20 is slidable relative to conduit 18 such that it may be extended beyond the distal end of conduit 18 and retracted back to be completely within conduit 18. FIGS. 7A and 7B further illustrate conduit stops 28 attached to conduit 18 and tool stops 30 attached to tool 20. Conduit stops 28 and tool stops 30 are arranged such that tool stops 30 cannot be slid distally past the location of conduit stops 28, as illustrated in FIG. 7B. In this manner, tool stops 30 and conduit stops 28 prevent tool 20 from being extended indefinitely beyond the distal end of conduit 18. In one embodiment, tool stops 30 may be adjusted longitudinally along tool 20 to control the maximum allowed extension of tool 20 beyond the distal end of conduit 18. Locating conduit stops 28 near the distal region of conduit 18 may improve the accuracy of control over the maximum extended position of tool 20 due to inexact displacement of tool 20 throughout the length of conduit 18. However, conduit stops 28 may be located at any point along conduit 18.

Referring again to FIG. 6, in the illustrated embodiment, support arms 16 merge and are coupled to one another at a region at or near the distal end of support arms 16 to form cage 14. In another embodiment illustrated in FIG. 8, support arms 16 merge with the distal end of shaft 26 and are coupled to shaft 26. One purpose of shaft 26 is to provide sufficient columnar strength to catheter 10 to enable catheter 10 to be easily steered down the vasculature. Materials with sufficient columnar strength include polymeric materials that may be reinforced with a braided or coiled metal material. Shaft 26 may be hollow to accommodate a guidewire.

Figure 8:
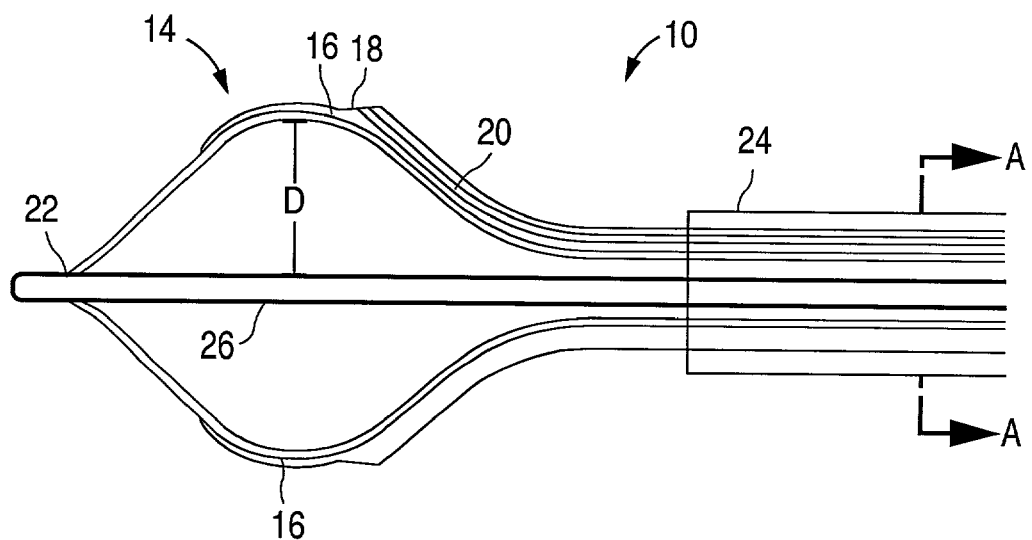
FIG. 8 is a sectional side view of one embodiment of the invention.
Figure 9:
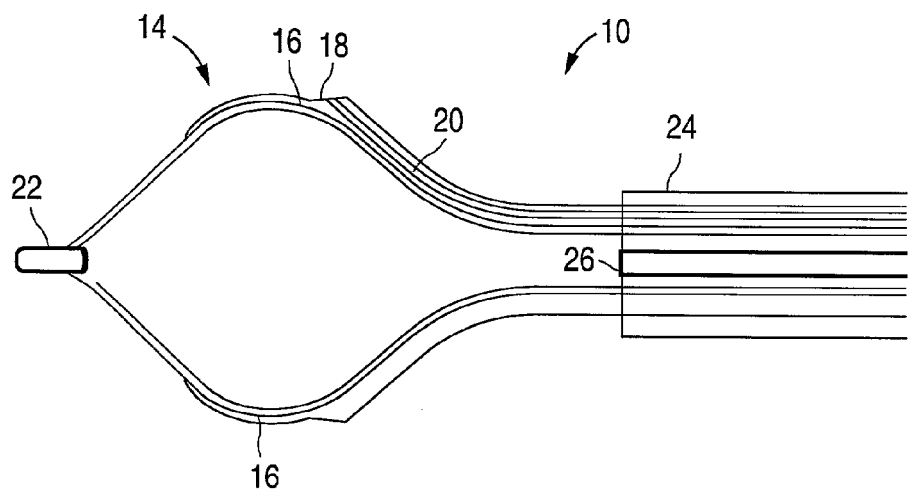
FIG. 9 is a sectional side view of one embodiment of the invention.

In an embodiment illustrated in FIG. 9, shaft 26 is truncated, terminating at the distal end of holder 24. Support arms 16 merge and the distal ends of support arms 16 are coupled to tip 22. An advantage of the embodiment illustrated in FIG. 9 is that while shaft 26 provides columnar strength to catheter 10, cage 14 has a smaller cross-section and is more flexible than an embodiment where shaft 26 extends to the distal ends of support arms 16, such as in FIG. 8. Another advantage of the embodiment illustrated in FIG. 9 is that shaft 26 is not required to stretch during the retraction of cage 14, as described below. In embodiments where support arms 16 are attached to shaft 26 or to tip 22, such as the embodiments pictured in FIG. 8 and FIG. 9, respectively, support arms 16 can be attached to shaft 26 or tip 22 using, for example, a heat treatment method or an adhesive. Both shaft 26 and tip 22 can be hollow to accommodate a guidewire.

Figure 10A:
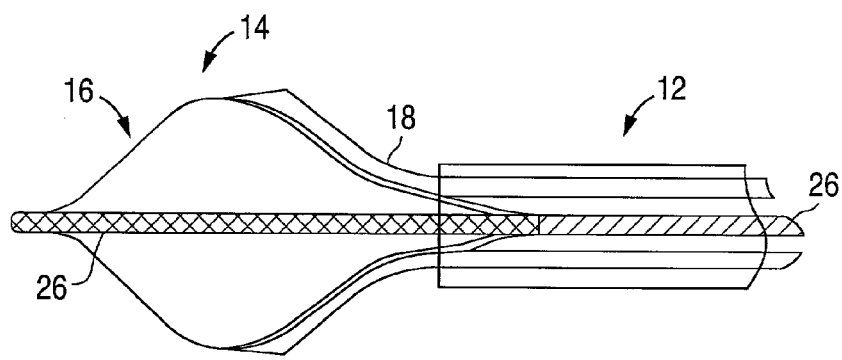
FIG. 10A is a sectional side view of one embodiment of the invention with the cage in a deployed state.
Figure 10B:
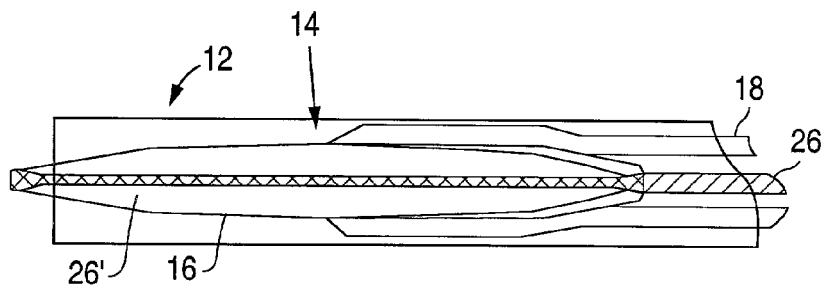
FIG. 10B is a sectional side view of one embodiment of the invention with the cage in a retracted state.

Elasticity is an important consideration for the material used to construct shaft 26. In the embodiment illustrated in FIGS. 10A and 10B, a section of shaft 26 may be required to stretch along its longitudinal axis during deployment of cage 14 since the proximal and distal ends of cage 14 are both attached to shaft 26. FIG. 10A illustrates cage 14 in a deployed position, and shaft 26 in an unstretched position. FIG. 10B illustrates that when cage 14 is retracted, a section of shaft 26 may be required to stretch and become thinner. The section of shaft 26 required to stretch may be made from an elastic material such as a polymeric material, or the entire length of shaft 26 may be made from an elastic material such as a polymeric material.

Figure 11A:
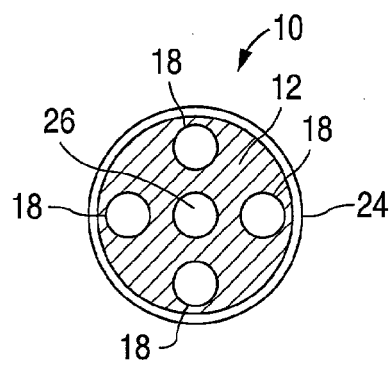
FIG. 11A is a cross-sectional view along the line A—A of FIG. 8.

FIG. 11A illustrates a cross-sectional view of FIG. 8 taken along the line A—A. In the illustrated embodiment, conduits 18 and shaft 26 extend longitudinally along at least the entire length of elongate tubular member 12, which can be, for example, between 100 and 200 cm long, to allow catheter 10 to be inserted into the vasculature of a patient. Elongate tubular member 12 may not be attached to conduits 18 or shaft 26 so that conduits 18 and shaft 26 can be slid telescopically within elongate tubular member 12, which allows for the expansion and retraction of cage 14. As previously described, shaft 26 provides longitudinal stability for catheter 10, allowing catheter 10 to be easily advanced through the vasculature. However, the flexibility of catheter 10 may decrease due to the added stability of shaft 26.

Figure 11B:
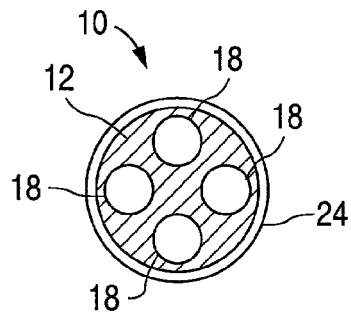
FIG. 11B is a cross-sectional view along the line B—B of FIG. 6.

FIG. 11B illustrates a cross-sectional view of FIG. 6 taken along the line B—B. In the illustrated embodiment, catheter 10 may be constructed without shaft 26, which can reduce the cross-sectional profile and increase the flexibility of catheter 10. Conduits 18 may not be attached to elongate tubular member 12 so that they may be slid longitudinally relative to elongate tubular member 12. The absence of a shaft requires that catheter 10 have enough stiffness to be pushed down the vasculature. Methods and materials for accomplishing this balance of flexibility and stiffness for a catheter are known by one of ordinary skill in the art.

Figure 12A:
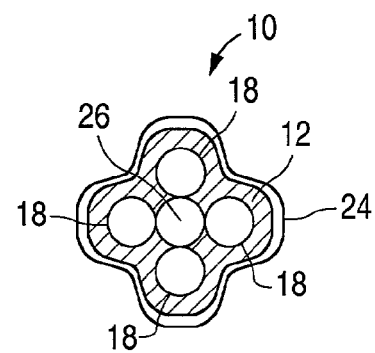
FIGS. 12A and 12B are cross-sectional views of two embodiments of the invention, one embodiment having a shaft and another embodiment lacking a shaft, respectively.
Figure 12B:
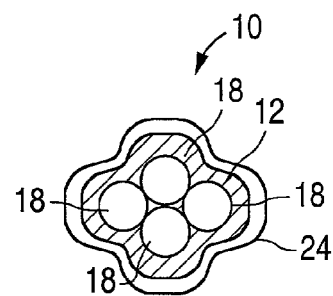

FIGS. 12A and 12B illustrate alternate embodiments of the cross-sections shown in FIGS. 11A and 11B, respectively. In FIG. 12A, conduits 18 and shaft 26 can be attached to each other but not to elongate tubular member 12 so that they may be slid together through a central lumen of elongate tubular member 12. In FIG. 12B, conduits 18 may be attached to each other but not to elongate tubular member 12 so that they may be slid together through a central lumen of elongate tubular member 12. In both of these illustrated embodiments, conduits 18 may be made from a material that allows conduits 18 to collapse in diameter when tool 20 is not in the lumen of conduit 18. Collapsed conduits 18 will then take up less space within catheter 10, so that catheter 10 will have a smaller overall diameter when tools 20 are not in the lumens of conduits 18. Collapsible conduits 18 may also render catheter 10 more flexible. The benefits of increased flexibility and smaller diameter are well-known to those skilled in the art and include access to tortuous vascular anatomy.

The choice of tool 20 is limited only by the ability of tool 20 to be inserted into conduit 18 and deployed down the length of conduit 18. Examples of suitable tools include, but are not limited to, needles, optical fibers, ultrasonic transducers, and RF electrodes. Catheter 10 may be used for any treatment method including for example, delivery of growth factors or other angiogenic factors using a needle, or delivery of DNA for gene therapy treatments. Further, catheter 10 can be used to deliver other bioactive agents to a body cavity. Catheter 10 may also be used in anti-arrhythmia treatments in which tool 20 is an electrode used to make selectively placed burns on the heart tissue.

FIGS. 13A, 13B, 14 and 15 illustrate one method of use of an embodiment of the present invention. In this case, catheter 10 has been inserted into patient 100 such that cage 14 can be deployed inside left ventricle 106. Minimally invasive methods for accessing left ventricle 106 of patient 100 with a medical device such as a catheter are known to those having ordinary skill in the art. Catheter 10 may be used to deliver and support tools within any body cavity, such as, but not limited to the cranium, the abdomen or body organs other than the heart.

Figure 13A:
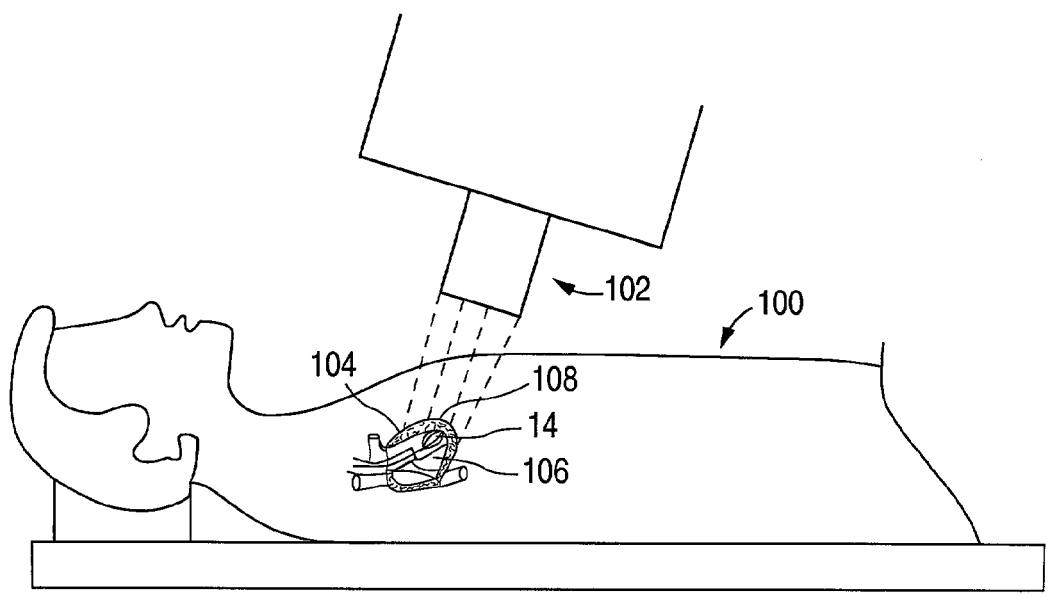
FIG. 13A illustrates a patient and the patient's heart with one embodiment of the invention deployed within the heart. An imaging device is positioned outside the patient and targeted at the treatment area in the heart.
Figure 13B:
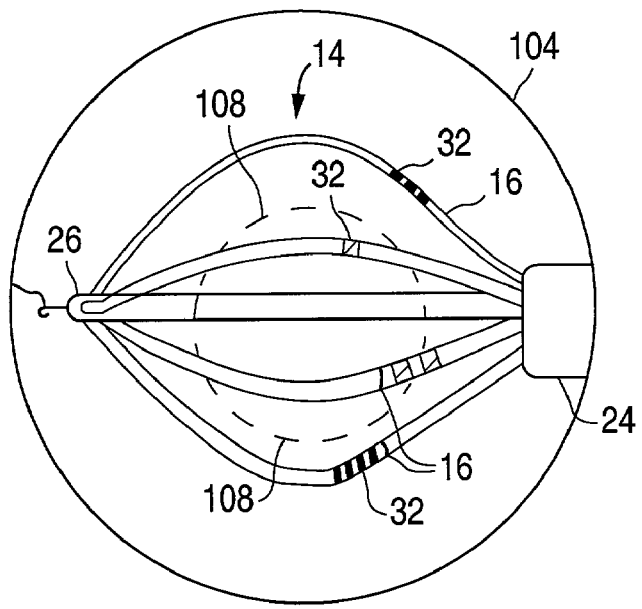
FIG. 13B is an enlarged view of the distal end of the invention deployed within the patient from FIG. 13A.

An imaging device 102 is typically used to monitor the treatment of patient 100. Typically, imaging device 102 is a fluoroscope, but can also be a magnetic resonance imager or another device suited to medical imaging. FIGS. 13A and 13B illustrate that imaging device 102 creates field of view 104 in which the progress of the treatment can be observed. Field of view 104 encompasses treatment area 108. A feature of this embodiment is the ability of a physician to precisely position cage 14 with respect to treatment area 108. Markers 32 on support arms 16 allow for identification and positioning of cage 14 within left ventricle 106.

While catheter 10 is maneuvered through the vascular system of patient 100, cage 14 is typically in the retracted position within holder 24 in the embodiment where holder 24 is used. Once at the desired location, cage 14 is deployed by sliding support arms 16 through and out of the distal end of holder 24. In its expanded position, cage 14 is capable of stabilizing and anchoring catheter 10 against the wall of left ventricle 106. This facilitates the precise delivery of tools 20 to treatment area 108. The deployed cage size can be controlled by limiting how much of cage 14 extends out of holder 24. Alternately, cages with specific deployed sizes and shapes can be used depending on the size and type of body cavity requiring treatment.

Figure 14:
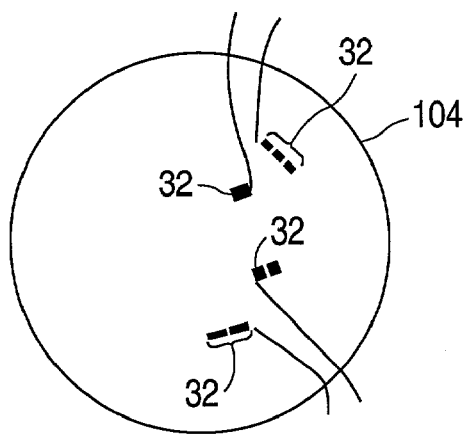
FIG. 14 illustrates the view through the imaging device of FIG. 13A.
Figure 15:
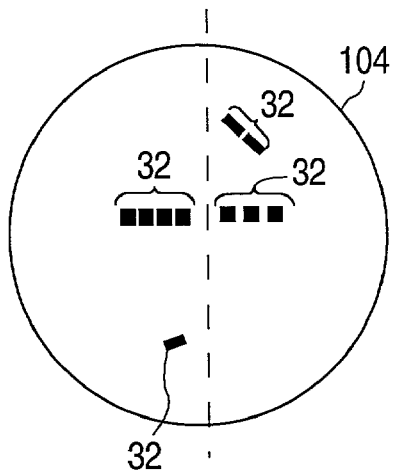
FIG. 15 illustrates the view through the imaging device of FIG. 13A after the markers have been aligned with the treatment area.

As illustrated in FIGS. 13B, 14, and 15, markers 32 are designed to be visualized in field of view 104, allowing the physician to position cage 14. The physician can identify the location of treatment area 108 based on assessment of the patient's disease and position imaging device 102 using known anatomical features. In one embodiment, markers 32 are placed at an area near the distal end of conduit 18. When markers 32 are near the distal end of conduit 18, a physician can determine the precise location of the distal end of conduit 18 with respect to treatment area 108 and thereby accurately deliver tools 20 to treatment area 108.

An exemplary view through imaging device 102 is illustrated in FIG. 14. Cage 14 has been extended so that support arms 16 are almost even with target treatment area 108. In this example, markers 32 correspond to individual support arms 16 as indicated in FIG. 13B. The imaging device is directly over treatment area 108 and markers 32 indicate the position of the distal ends of conduits 18. From the illustration in FIG. 14, none of the distal ends of conduits 18 are centered adjacent treatment area 108. Accordingly, cage 14 must be repositioned so that a subsequently deployed tool 20 would be directed to treatment area 108. In order to reposition cage 14, cage 14 may be partially or fully retracted and then rotated.

FIG. 15 illustrates the same view through imaging device 102 after cage 14 has been rotated and repositioned relative to treatment area 108. In FIG. 15, two sets of markers 32 are aligned, which indicates that the respective support arms 16 that correspond to these aligned markers 32 are also aligned. Because imaging device 102 is oriented over and in line with treatment area 108, aligned markers 32 indicated that cage 14 is positioned such that the distal end of corresponding conduit 18 is adjacent to treatment area 108. Having the distal end of corresponding conduit 18 adjacent treatment area 108 allows the physician to precisely deliver tool 20 to treatment area 108.

Although the Figures illustrate four support arms 16, cage 14 may included more support arms 16. In general, if cage 14 has more pairs of opposing support arms 16, it is easier to position the distal end of one conduit 18 adjacent to treatment area 108. With more support arms 16, it is more likely that one of support arms 16 is close to treatment area 108 during initial deployment of cage 14 such that less rotation and repositioning is required. However, more support arms 16 take up more space in catheter 10 and could restrict the ability of catheter 10 to navigate through certain parts of the anatomy.

In the embodiments illustrated in FIGS. 13A, 13B, 14, and 15, markers 32 not only identify the location of the distal ends of conduits 18, but also distinguish one support arm 16 from another support arm 16. In this manner, the physician may choose the appropriate conduit 18 to use to deliver tool 20. In order to facilitate deliver of tool 20, the proximal end of conduit 18 may be funnel shaped such that the diameter of conduit 18 is larger at its proximal end. The use of a funnel shape at the proximal end of conduit 18 allows the physician to introduce tool 20 into the lumen on conduit 18 without undue difficulty.

While particular embodiments of the present invention have been shown and described, it will be clear to those of ordinary skill in the art that changes and modifications can be made without departing from the broad aspects of the invention. Therefore, the claims are to encompass all such changes and modifications as falling within the scope of the invention.

What is claimed is:

1. A medical device, comprising:
    an elongate tubular member for inserting into a body cavity or organ of a patient;
    at least two support arms capable of extending out from and retracting into the distal end of the elongate tubular member, the support arms converging at the distal end of the support arms and being outwardly bow-shaped when extended out from the elongate tubular member;
    a tool for performing a therapeutic or diagnostic function extending at least partially along one of the support arms; and
    a conduit extending at least partially along the support arm along which the tool extends, wherein the conduit houses the tool, the tool being configured to extend out from and retract into the conduit.

2. The medical device of claim 1, additionally including a first stop attached to the inner surface of the conduit and a second stop attached to the tool, wherein the tool can be extended out from the conduit until the second stop contacts the first stop.

3. The medical device of claim 1, wherein the distal end of the elongate tubular member includes a segment having a larger diameter than the remaining portion of the elongate tubular member.

4. The medical device of claim 1, wherein the support arms bend to a generally linear shape from the bow-shape configuration when the support arms are retracted into the tubular member.

5. The medical device of claim 1, additionally including a shaft slidably disposed at least partially along the tubular member.

6. The medical device of claim 5, wherein the shaft includes a lumen for receiving a guidewire.

7. The medical device of claim 5, wherein the distal ends of the support arms converge by being attached to the shaft such that the slidable movement of the shaft along the elongate tubular member extends and retracts the support arms out from and into the elongate tubular member.

8. The medical device of claim 1, additionally including a tip member, wherein the distal ends of the support arms converge by being attached to the tip member.

9. The medical device of claim 1, wherein the distal ends of the support arms are coupled to one another.

10. The medical device of claim 1, wherein the support arms are made from an elastic material allowing the support arms to flex into a generally linear configuration from the bow-shaped configuration when the support arms are retracted into the elongate tubular member and allowing the support arms to bend back into the bow-shaped configuration when the support arms are extended out from the tubular member.

11. The medical device of claim 1, wherein the support arms are capable of being rotated with respect to the elongate tubular member.

12. The medical device of claim 1, wherein the support arms support markers for allowing a physician to locate the position of the support arms using an imaging apparatus.

13. The medical device of claim 1, wherein one of the support arms supports a marker having a different shape than a marker supported by another support arm.

14. The medical device of claim 1, wherein one of the support arms supports more markers than another support arm.

15. The medical device of claim 1, wherein the tool is a needle for delivering a therapeutic substance, an ultrasound transducer, an electrode, an optical fiber, or a laser system.

16. The medical device of claim 1, wherein the conduit is capable of collapsing to a reduced diameter when the tool is not in the conduit.

17. A medical device, comprising:
    a catheter;
    a set of support arms integrated with the catheter, each support arm being capable of bending from a linear configuration into an outwardly curved configuration when the support arms are pushed out of the distal end of the catheter and capable of bending back into a linear configuration from the outwardly curved configuration when the support arms are retracted back into the distal end of the catheter;
    a conduit extending at least partially along one of the support arms; and
    a therapeutic or diagnostic tool slidably disposed within the conduit, the tool capable of being extended out from and retracted back into the conduit.

18. The device of claim 17, wherein the support arms are connected to one another at the distal end of each of the support arms.

19. A method for performing a therapeutic or diagnostic treatment, comprising:
    inserting a catheter into the patient;
    extending a set of support arms out from one end of the catheter, wherein the support arms bow in an outward direction to anchor the catheter to the desired area of treatment; and
    extending a therapeutic or diagnostic tool from a conduit disposed at least partially along one of the support arms to perform a therapeutic or diagnostic procedure.

20. A medical device, comprising:
    an elongate tubular member for inserting into a body cavity or organ of a patient;
    at least two support arms capable of extending out from and retracting into the distal end of the elongate tubular member, the support arms having an outwardly projecting-shaped when extended out from the elongate tubular member;
    a shaft connected to the support arms and configured to be slidably disposed within the distal end of the elongated tubular member such that the movement of the shaft out from and into the elongated tubular member allows the extension and retraction of the support arms out from and into the elongated member, wherein the shaft is made from a flexible material that allows for the shaft to stretch during retraction of the shaft into the elongated tubular member; and a tool for performing a therapeutic or diagnostic function extending at least partially along one of the support arms.

21. A medical device, comprising:

an elongate tubular member for inserting into a body cavity or organ of a patient;

at least two support arms capable of extending out from and retracting into the distal end of the elongate tubular member, the support arms having an outwardly bow-shaped configuration when extended out from the elongate tubular member;

a re-enforcement member coupled to at least on of the support arms to add stiffness to the support arm; and a tool for performing a therapeutic or diagnostic function extending at least partially along one of the support arms.

22. A medical device, comprising:

an elongate tubular member for inserting into a body cavity or organ of a patient;

at least two support arms capable of extending out from and retracting into the distal end of the elongate tubular member, the support arms having an outwardly projecting-shape when extended out from the elongate tubular member;

markers supported by the support arms to allow a physician to locate the position of the support arms by an imaging apparatus, wherein (i) a marker of one support arm has a different shape than a marker of another support arm; or (ii) one of the support arms has a different number of markers that the other support arm; and a tool for performing a therapeutic or diagnostic function extending at least partially along one of the support arms.

23. A medical device, comprising:

an elongate tubular member for inserting into a body cavity or organ of a patient;

support arms capable of extending out from and retracting into the distal end of the elongate tubular member, the support arms converging at the distal end of the support arms and having an outwardly projected-shaped when extended out from the elongate tubular member;

a tool for performing a therapeutic or diagnostic function extending at least partially along one of the support arms; and wherein the support arms are capable of being rotated as a unit with respect to the elongated tubular member so as to allow the physician to reposition the tool.

24. A medical device, comprising:

a tubular member for inserting into a body cavity or organ of a patient;

support arms capable of extending out from and retracting into the distal end of the tubular member, the support arms having an outwardly projected-shape when extended out from the elongate tubular member;

a conduit line integrated with at least one of the support arms; and a tool for performing a therapeutic or diagnostic function integrated with the conduit.

* * * * *